United States Patent
Thompson et al.

(10) Patent No.: US 11,253,614 B2
(45) Date of Patent: Feb. 22, 2022

(54) METHODS FOR DETECTING AND/OR PREDICTING AGE-RELATED MACULAR DEGENERATION AND/OR ALZHEIMER'S DISEASE

(71) Applicants: University of Maryland, Baltimore, Baltimore, MD (US); THE QUEEN'S UNIVERSITY OF BELFAST, Belfast (GB)

(72) Inventors: Richard Thompson, Baltimore, MD (US); Huihui Zeng, Ellicott City, MD (US); Henryk Szmacinski, Sykesville, MD (US); Imre Lengyel, Belfast (NF)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 528 days.

(21) Appl. No.: 16/326,793

(22) PCT Filed: Aug. 17, 2017

(86) PCT No.: PCT/US2017/047323
§ 371 (c)(1),
(2) Date: Feb. 20, 2019

(87) PCT Pub. No.: WO2018/039030
PCT Pub. Date: Mar. 1, 2018

(65) Prior Publication Data
US 2021/0283275 A1  Sep. 16, 2021

Related U.S. Application Data

(60) Provisional application No. 62/378,268, filed on Aug. 23, 2016.

(51) Int. Cl.
A61B 5/00 (2006.01)
A61B 3/12 (2006.01)
(Continued)

(52) U.S. Cl.
CPC ............ *A61K 49/0021* (2013.01); *A61B 3/12* (2013.01); *A61B 5/1455* (2013.01); *A61B 5/14546* (2013.01)

(58) Field of Classification Search
CPC .... A61B 3/00; A61B 3/12; A61B 3/13; A61B 5/00; A61B 5/0059; A61B 5/0071;
(Continued)

(56) References Cited

U.S. PATENT DOCUMENTS 7,374,746 B2  5/2008  Frangioni
9,801,955 B2  10/2017  Thompson et al.
(Continued)

FOREIGN PATENT DOCUMENTS

WO  9517673 A1  5/1995
WO  0052479     9/2000
(Continued)

OTHER PUBLICATIONS

Krueger, Christel et al.; "Tetracycline derivatices: alternative effectors for Tet transregulators," BioTechniques, 2004 37:546-550.
(Continued)

*Primary Examiner* — Chu Chuan Liu
(74) *Attorney, Agent, or Firm* — Tristan A. Fuierer; Olive Law Group, PLLC

(57) ABSTRACT

The present invention provides for the use of hydroxyapatite-selective fluorescent dyes in combination with fluorescence lifetime imaging to detect any hydroxyapatite spherules or hydroxyapatite deposits in the retina tissue of a subject, including the peripheral or macula tissue, wherein the hydroxyapatite spherules or hydroxyapatite deposits initiate or support the growth of sub-RPE deposits and correlates with age-related macular degeneration and/or Alzheimer's disease.

10 Claims, 10 Drawing Sheets

(51) Int. Cl.
*A61K 49/00* (2006.01)
*A61B 5/145* (2006.01)
*A61B 5/1455* (2006.01)

(58) Field of Classification Search
CPC ... A61B 5/145; A61B 5/1455; A61B 5/14551; A61B 5/14532; A61B 5/14555; A61B 5/14546; A61B 5/14556
See application file for complete search history.

(56) References Cited

U.S. PATENT DOCUMENTS

| | | |
|---|---|---|
| 2006/0099714 A1 | 5/2006 | Mata et al. |
| 2009/0123383 A1 | 5/2009 | Frangioni |
| 2016/0278677 A1 | 9/2016 | Kerbage et al. |
| 2016/0287614 A1 | 10/2016 | Mandhare et al. |

FOREIGN PATENT DOCUMENTS

| | | |
|---|---|---|
| WO | 0238190 A2 | 5/2002 |
| WO | 2006047475 A2 | 5/2006 |
| WO | 2009108704 A1 | 9/2009 |
| WO | 2010116132 A2 | 10/2010 |
| WO | 2014036483 A1 | 3/2014 |
| WO | 2015072964 A1 | 5/2015 |
| WO | 2015075640 A1 | 5/2015 |

OTHER PUBLICATIONS

Supplementary European Search Report, dated Mar. 12, 2020.
Lim, L.S., et al.; "Age-related macular degeneration," The Lancet, 379, pp. 1728-1738, doi:http://dx.doi.org/10.1016/S0140-6736(12)60282-7, 2012.
Sarks, S.H.; Aging and degeneration in the macular region: a clinico-pathological study. The British Journal of Ophthalmology, 60, pp. 324-341, 1976.
Sarks, S.H., et al.; "Early drusen formation in the normal and aging eye and their relation to age related maculopathy: a clinicopathological study," The British Journal of Ophthalmology, 83, pp. 358-368, 1999.
Pauleikhoff, D., et al.; "Aging changes in Bruch's membrane. A Histochemical and morphologic study," Ophthalmology, 97, pp. 171-178, 1990—Abstract Only.
Pauleikhoff, D., et al.; "Drusen as risk factors in age-related macular disease," American Journal of Ophthalmology, 97, pp. 38-43, 1990—Abstract Only.
Lengyel, I., et al.; "Association of drusen deposition with choroidal intercapillary pillars in the aging human eye," Invest Ophthalmol Vis Sci, 45, pp. 2886-2892, 2004.
Giachelli, C.M.; "Ectopic calcification: gathering hard facts about soft tissue mineralization," The American Journal of Pathology, 154, pp. 671-675, doi:101016/S0002-9440(10)65313-8, 1999.
Davis, W.L.; et al.; "An electron microscopic histochemical and analytical x-ray microprobe study of calcification in Bruch's membrane from human eyes," The Journal of Histochemistry and Cytochemistry: official Journal of hte Histochemistry Society, 29, pp. 601-608, 1981.
Vogt, S.D., et al.; "Retinal pigment epithelial expression of complement regulator CD46 is altered early in the course of geographic atrophy," Experimental Eye Research 93, pp. 413-423, doi:101016/j.exer.2011.06.002, 2011.
Raggatt, L.J., et al.; "Cellular and molecular mechanisms of bone remodeling ," The Journal of Biological Chemistry, 285, pp. 25103-25108, doi:10.1074/jbc.R109.041087, 2010.
Skinner, H.C., et al.; "Tetracyclines and mineralized tissues: review and perspectives," Yale J Biol Med, 48, pp. 377-397, 1975.
Kovar, J.L., et al.; Near-infrared-labeled tetracycline derivative is an effective marker of bone deposition in mice. Anal Biochem, 416, pp. 167-173, doi:10.1016/j.ab.2011.05.011, 2011.
Vilmann, H.; "The in vivo staining of bone with alizarin res S," J Anat, 105, pp. 533-545, 1969.
Rahn, B.A., et al.; "Xylenol orange, a fluorochrome useful in polychrome sequential labeling of calcifying tissues," Stain Technol, 46, pp. 125-129, 1971, Abstract Only.
Mullins, R.F., et al.; "Drusen associated with aging and age-related macular degeneration contain proteins common to extracellular deposits associated with altherosclerosis, elastosis, amyloidosis, and dense deposit disease," Faseb J, 14, pp. 835-846, 2000, Abstract Only.
Hageman, G.S., et al.; "Molecular composition of drusen as related to substructural phenotype," Mol Vis, 5, 28, 1999.
Russell, S.R., et al.; "Location, substructure, and composition of basal laminar drusen compared with drusen associated with aging and age-related macular degeneration," American journal of Ophthalmology, 129, 205-214, 2000.
Curcio, C.A., et al.; "Accumulation of cholesterol with age in human Bruch's membrane," Invest Ophthalmol Vis Sci, 42, pp. 265-274, 2001.
Raggio, C.L., et al.; "In vivo hydroxyapatite formation induced by lipids," J Bone Miner Res, 1, pp. 409-415, doi:10.1002/jbmr.5650010505, 1986.
Pecorella, I., et al.; "A scanning transmission microscopy and energy-dispersive x-ray microanalysis of idiopathic ocular calcification and oxalosis in AIDS patients," Ultrastruct Pathol, 23, 223-231, 1999.
Spraul, C.W., et al.; "Characteristics of Drusen and Bruch's membrane in postmortem eyes with age-related macular degeneration," Archives of Ophthalmology, 115, pp. 267-273, 1997.
Ulshafer, R.J., et al.; "Scanning electron microscopy of human drusen," Investigative ophthalmology & Visual Science, 28, pp. 683-689, 1987.
Ulshafer, R.J., et al.; "Distributions of elements in the human retinal pigment epithelium," Archives of Ophthalmology, 108, pp. 113-117, 1990.
Van Der Schaft, T.L., et al.; "Element analysis of the early stages of age-related macular degeneration," Archives of Ophthalmology, 110, 389-394, 1992.
International Search Report, dated Dec. 19, 2017.

METHODS FOR DETECTING AND/OR PREDICTING AGE-RELATED MACULAR DEGENERATION AND/OR ALZHEIMER'S DISEASE

CROSS REFERENCE TO RELATED APPLICATION

This application is filed under the provisions of 35 U.S.C. § 371 and claims the priority of International Patent Application No. PCT/US2017/047323 filed on 17 Aug. 2017 entitled "METHODS FOR DETECTING AND/OR PREDICTING AGE-RELATED MACULAR DEGENERATION AND/OR ALZHEIMER'S DISEASE" in the name of Richard Thompson, et al., which claims priority to U.S. Provisional Patent Application No. 62/378,268, filed on 23 Aug. 2016, both of which are hereby incorporated by reference herein for all purposes.

BACKGROUND OF THE INVENTION

Field of the Invention

The present invention relates to predicting, detecting, and diagnosing age-related macular degeneration (AMD), Alzheimer's disease (AD) and other diseases associated with hydroxyapatite-containing deposits in the retina. In particular, the presently disclosed invention provides for compositions and methods of identifying the presence of hydroxyapatite (HAP) and/or HAP spherules that are involved in protein deposition in the sub-retinal pigment epithelium (RPE) and contribute to the growth of sub-RPE deposits associated with AMD and/or AD.

Description of Related Art

Age-related macular degeneration (AMD) is the most common cause of legal blindness in developed countries, affecting over ten million people in the United States. There is no cure for AMD and although the 15% of cases comprising the most destructive, "wet" form of AMD can be slowed by treatment with VEGF inhibitors, for 85% of cases there is currently no treatment, and most patients present with irreversible vision loss.

Accumulation of protein- and lipid-containing deposits external to the retinal pigment epithelium (RPE) is common in the aging eye, and has long been viewed as the hallmark of age-related macular degeneration (AMD) and/or Alzheimer's disease. In the eye, the Bruch's membrane (BM), which is interposed between the retinal pigment epithelium (RPE) and choroid, becomes thickened with age. This thickening is associated with accumulation of deposits, termed generally as sub-RPE deposits, that may be focal (recognized clinically as sub-retinal deposits or drusen) or diffuse (basal laminar or linear deposits, depending on whether they are present internal or external to the RPE basement membrane). These deposits contain several different proteins derived from sources both in the retina and the serum, notably including beta-amyloid, complement factor H, serum albumin, vitronectin, apolipoprotein E, and crystallins; some of these proteins are known to avidly bind metal ions such as zinc. The process occurs maximally in the macula, the locus of highest resolution vision, and is integral to the pathogenesis of age-related macular degeneration (AMD) but remains poorly understood.

Due to this correlation between AMD and sub-RPE deposit formation, substantial effort has been devoted to determining the composition and origin of sub-RPE deposits, with a view to developing better diagnosis, prevention, and treatment for AMD (1). Although AMD does not necessarily follow the same course in all patients, it is acknowledged that progression of sub-RPE deposit formation is a major factor in a large proportion of cases.

Several therapies are in development or trials for treatment of AMD, however, to be most effective these treatments should be started before damage has occurred. Thus, an early diagnostic or screening tool is desirable. While many diagnostic tools are available to the ophthalmologist, none offers detection of the disease before damage has occurred. Thus, it would be advantageous to provide a diagnostic method for early detection.

SUMMARY OF THE INVENTION

The present invention provides for the use of hydroxyapatite-selective fluorescent dyes in combination with the use of a fluorescence lifetime imaging device for early detection of hydroxyapatite (HAP) spherules or HAP deposits in the retina of a subject, including the peripheral and/or macula tissue, wherein the HAP spherules or HAP deposits initiate or support the growth of sub-RPE deposits and correlate with age-related macular degeneration and/or Alzheimer's disease. "Fluorescence lifetime" as used herein broadly refers to the commonly understood emissive lifetime of the photoluminescent species, being the average time the photoluminescent species spends in the excited state between excitation and emission of the photoluminescence, and thus the inverse of the emissive rate. Many common organic photoluminescent species including molecules such as fluorescein or rhodamine exhibit lifetimes in the nanosecond regime, whereas other photoluminescent species known to the art, including metal ion complexes such as Ru(bipy)$_3$ or lanthanide chelates, may exhibit longer lifetimes in the microsecond to second range, or certain organic fluorophores such as cyanines or Rose Bengal may exhibit shorter lifetimes, in the picosecond regime.

In one aspect the present invention provides for a method of detecting and/or diagnosing age-related macular degeneration or Alzheimer's disease in retina tissue of a subject, the method comprising:

a. administering a hydroxyapatite-selective fluorescent dye to the retina tissue in an amount sufficient for binding to any hydroxyapatite (HAP) deposits or spherules in the retina tissue to form a HAP/hydroxyapatite-selective fluorescent complex;

b. irradiating the HAP/hydroxyapatite-selective fluorescent complex with electromagnetic radiation in an amount sufficient to excite the hydroxyapatite-selective fluorescent dye complex; and c. monitoring and/or measuring the lifetime of a fluorescent signal of the HAP/hydroxyapatite-selective fluorescent complex with a fluorescence lifetime imaging device, wherein the hydroxyapatite-selective fluorescent dye complex exhibits a longer fluorescence lifetime signal relative to background fluorescence of retina tissue, thereby indicating detection or diagnosis of age-related macular degeneration or Alzheimer's disease.

The step of monitoring and/or measuring the lifetime of a fluorescent signal of the HAP/hydroxyapatite-selective fluorescent complex can be conducted by fluorescence lifetime imaging devices employing time and frequency domain technologies, time-correlated single photon counting, time-gated photon counting with laser scanning, streak cameras, point scanning and wide-field imaging techniques, such as a modulated charge-coupled device, and discussed by Becker (6) and commercially available.

In the time domain, a short pulse of electromagnetic radiation is used to irradiate the HAP/hydroxyapatite-selective fluorescent complex and the subsequent fluorescence emission is recorded as a function of time and usually in a nanosecond time frame. Time domain data may be collected by, for example, streak cameras, boxcar integrator, and Time-Correlated Single-Photon Counting (TCSPC). In the frequency domain, the HAP/hydroxyapatite selective fluorescent complex is excited by an amplitude-modulated source of electromagnetic energy. The amplitude-modulated excitation may be modulated in a sinusoidal waveform, or a series of pulses, and the modulation frequency is typically within one-hundred fold of the emissive rate. The emission waveform is demodulated and phase-shifted with respect to the excitation waveform. For a single emitting photoluminescent species, the lifetime is a simple function of the frequency and measured phase shift or demodulation. Imaging, devices including microscopes and ophthalmoscopes that produce images whose contrast is derived from differences in fluorescence lifetime in the specimen being imaged have been described using both time- and frequency-domain approaches (or both) and some are commercially available. Some employ scanning excitation with point detectors and TCSPC or time-gated detection, others in the frequency domain employ point detectors with scanning excitation, or a camera with modulated gain.

In the present invention the hydroxyapatite-selective fluorescent dye is preferably a tetracycline, a tetracycline derivative or combinations thereof that may include, but are not limited to, chlortetracycline, demeclocycline, doxycycline, methacycline, oxycycline, anhydrochlortetracycline, anhydrotetracycline, cetocycline and chelocardin. Oxytetracycline and doxycycline are approved for intravenous application in humans by the Federal Drug Administration (FDA). As used herein, the term "tetracycline derivative" includes tetracycline as well as its derivatives. Demeclocycline, methacycline, tetracycline, oxytetracycline and doxycycline are approved for oral delivery. Chlortetracycline is only approved for a local topical administration, but was previously administered orally. Other hydroxyapatite-selective fluorescent dyes may include, but are not limited to, Alizarin Red S, Xylenol Orange, LiCor Bone Tag 680 RD and Osteosense 680EX. However, any of the aforementioned compounds may be delivered orally, topically, or intravenously to detect retinal HAP deposits as described herein.

In another aspect the present invention provides for a method for predicting or diagnosing age-related macular degeneration and/or Alzheimer's disease in a subject by detecting HAP deposits in the retina tissue of the subject, the method comprising:
a. administering a tetracycline derivative to the subject in an amount sufficient for binding to any HAP deposits in the retina tissue of the subject;
b. irradiating the retina tissue with electromagnetic radiation in an amount sufficient to excite the tetracycline derivative;
c. scanning the retina tissue of the subject a fluorescence lifetime imaging device;
d. measuring/monitoring the lifetime of fluorescent signal of any bound tetracycline derivative to HAP deposits;
e. obtaining a profile of HAP deposits in the subject's retina, wherein the HAP deposits bound to the tetracycline derivative exhibits a longer lifetime compared to background tissue; and
f. using the obtained profile to diagnose or predict age-related degeneration and/or Alzheimer's disease in the subject.

It has been found that the background fluorescence of scanned retina tissue has a fluorescence lifetime from about 0.4 to about 0.7 nsec and the tetracycline derivative bound to HAP deposits has a fluorescence lifetime from about 1.2 to about 6 nsec depending on the specific tetracycline derivative. For example, chlortetracycline's range bound to HAP is about 1.4 to 1.9 nsec, but doxycycline's range is 3.5 to 4.2 nsec. Such comparison provides for identifying the amount and progression of HAP deposits forming in the retina tissue and such method provides for a method that does not include background fluorescence of scanned retina tissue.

Administering the tetracycline derivative to the subject can be effected by topical application to the eye of a subject, orally or injection. Topical application may include eye drop formulations comprising the tetracycline derivative. In the alternative, a solution comprising the tetracycline derivative may be injected into vitreous humor within the eye of the subject.

In a still further aspect, the present invention provides for a method of monitoring the level of HAP deposits in a subject at risk for macular degeneration or Alzheimer's disease, the method comprising:
a. administering a tetracycline derivative to the subject in an amount sufficient for binding to any HAP deposits in the retina of the subject;
b. irradiating the tetracycline derivative with electromagnetic radiation in an amount sufficient to excite the tetracycline derivative;
c. scanning the retina of the subject with a fluorescence lifetime imaging device;
d. measuring and monitoring the lifetime of a fluorescent signal of any bound tetracycline derivative to HAP deposits relative to a fluorescent signal of unbound tetracycline derivative, wherein the fluorescent signal of any bound tetracycline derivative to HAP deposits is longer than an unbound tetracycline derivative; and
e. obtaining a profile of HAP deposits in the subject, and using the obtained profile to diagnose or predict age-related macular degeneration in the subject.

In yet another aspect the present invention provides for the identifying or labeling of drusen or HAP deposits in retina tissue to be used in diagnosing or predicting the likelihood of having or developing age-related macular degeneration and/or Alzheimer's disease, the method comprises:
a. administering a tetracycline derivative be retina tissue in an amount sufficient binding to any drusen or HAP deposits in the retina tissue;
b. irradiating the tetracycline derivative with electromagnetic radiation in an amount sufficient to excite the tetracycline derivative;
c. capturing the lifetime of a fluorescent signal or mean thereof of any bound tetracycline derivative to drusen or HAl deposits; and
d. obtaining a profile of drusen or HAP deposits n the retina tissue and using the obtained profile to predict age-related macular degeneration and/or Alzheimer's disease in the retina tissue.

Notably, the capturing of the lifetime of the fluorescent signal can also be conducted by a sonification plugin as an extension of the imaging device or in place thereof. Importantly, the fluorescent signal comprises light with specific frequencies, visible spectrum, infrared wavelengths or molecular vibrations that are emitted by the binding of a tetracycline derivative to HAP deposits and forming a pattern which can be convened into an audio signal. Different audio pitch, loudness, timbre, spatialization and temporal patterns of sound is assigned to each pattern, to be communicated through an algorithm to the practitioner. Preferably such audio signal is accomplished by a parameter mapping sonification method wherein a classification method and/or clustering algorithm is used to isolates clusters of data related to frequencies and length of such emission and such cluster of data is then assigned a unique sound. Such classification method may include but is not limited to raw weights classification, concept mapping classification and K-Means cluster analysis.

In another aspect, the present invention includes a step of generating an image based on the scanned retina and the observed fluorescent signal of any bound tetracycline derivative to HAP deposits. Such image can be compared with a set of controls, wherein controls include a series of profiles of different levels of HAP deposits representing a particular stage of age-related macular degeneration, including one that does not suffer from age-related macular degeneration.

In a still further aspect, the present invention provides for a method for identifying HAP deposits in peripheral retina tissue to be used diagnosing or predicting the likelihood of having or developing Alzheimer's disease, the method comprises:

a. administering a tetracycline derivative to the peripheral retina tissue in an amount sufficient for binding to any HAP deposits in the peripheral retina tissue;
b. irradiating the tetracycline derivative with electromagnetic radiation in an amount sufficient to excite the tetracycline derivative;
c. scanning the peripheral retina tissue with a fluorescence lifetime imaging device;
d. measuring the lifetime of a fluorescent signal of any bound tetracycline derivative to HAP deposits compared to a fluorescent signal of an unbound tetracycline derivative, wherein the fluorescent signal of any bound tetracycline derivative to HAP deposits exhibits a longer fluorescence lifetime signal than that of background fluorescence of the background tissue; and
e. obtaining a profile of HAP deposits in the peripheral retina tissue, and using the obtained profile to diagnose Alzheimer's disease.

Additionally, the present invention provides for methods for labeling or detecting HAP deposits. Embodied methods include contacting a tissue sample with a tetracycline derivative and detecting a signal from the tetracycline derivative after binding with HAP deposits. The presence of the signal from the tetracycline derivative indicates the presence of HAP deposits, such as drusen, sub-retinal deposits or combinations thereof.

Other hydroxyapatite-selective fluorescent dyes that exhibit a longer fluorescence lifetime than that of the background fluorescence of retina tissue may be used in the present invention including Alizarin Red S, Tetracycline, Xylenol Orange, Osteosense 680EX and LiCor Bone Tag 680RD.

Still further other fluorescent labels that bind to HAP and provide a signal may be tested to determine the fluorescence lifetime relative to the background fluorescence of retina tissue.

The present invention also provides for kits comprising a tetracycline derivative in pharmaceutically acceptable carrier. The pharmaceutically acceptable carrier can be an aqueous eye drop solution or a solution for injection into vitreous humor of the eye. For the eye drop solution, the container is configured, to administer a solution in a drop wise manner. The container can also be a syringe or other container. In the alternative, the tetracycline derivative may be formulated in an oral form, such as a tablet, capsule or solution.

Further features and advantages of the present invention will become evident to those of ordinary skill in the art after a study of the present application.

BRIEF DESCRIPTION OF THE DRAWINGS

FIG. 9 illustrates the principle of the phasor plot, where at 100 MHz modulation frequency a fluorophore with 0.8 nsec lifetime maps to a phase angle $\varphi$ of 28.7 degrees, and of modulation (length of the arc)=0.89 of.

DETAILED DESCRIPTION OF THE INVENTION

Figure 1:
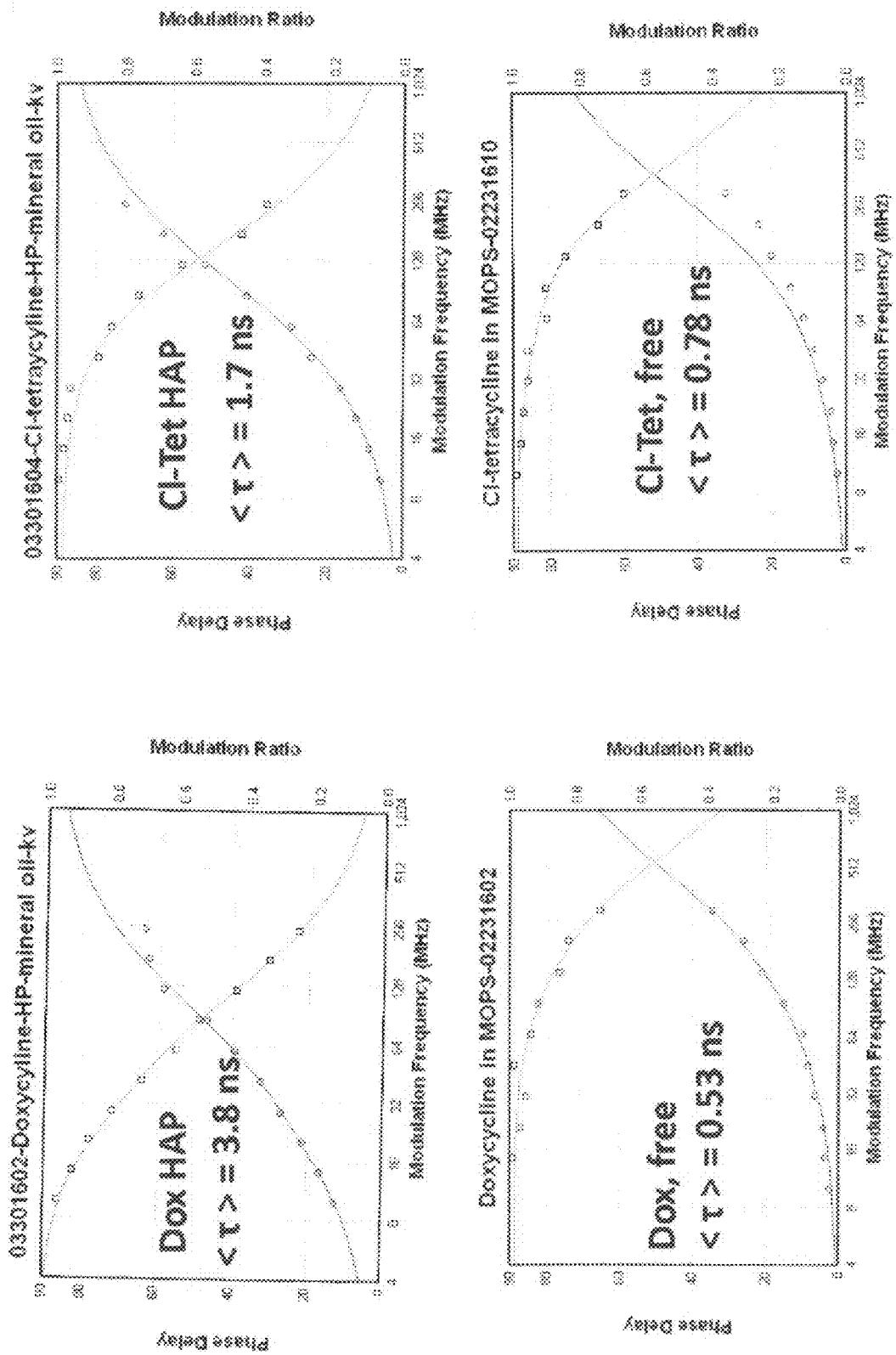
FIG. 1 shows Frequency-dependent phase and modulation data and best lit lines for Doxycycline (left panels) and Chlortetracycline (right panels) bound to HAP (upper panels) and free in solution (lower panels).

The present invention shows that deposits in the retina may be stained by a variety of tetracycline derivatives that exhibit changes, that being, an increase in their fluorescence upon binding to HAP, the hard mineral form of calcium phosphate found in bones and teeth (7). The present invention measures the life-time fluorescence of binding to HAP and overcomes the fluorescent interference ("background fluorescence") from pigment granules in the retinal pigment epithelium (RPE) layer of the retina and other portions of the retina.

Results from fluorescence lifetime imaging of the living retina (2) and many other tissues suggested that much of the background would have short fluorescence lifetimes (≤0.5 nsec). As such, the emission from a fluorescent label with a suitably longer lifetime could be resolved from shorter lifetime background fluorophores including in some cases, the fluorescent label unbound or nonspecifically bound, using the method of fluorescence lifetime imaging. Fluorescence lifetime imaging creates fluorescence images wherein the contrast of the image arises not from differences in emission intensity, but rather differences in fluorescence lifetime (3). Imaging devices are available with this capability from ISS, Inc., Urbana, Ill.; Nikon, Inc., Garden City, N.Y.; and PicoQuant GmbH, Berlin, Germany.

Thus, the present invention provides for early screening and imaging of HAP in the retina, that being the peripheral retina or the macula, to predict or diagnose age-related macular degeneration and/or Alzheimer's disease, by imaging any HAP deposits in the retina stained preferably by a tetracycline derivative and using a fluorescence ophthalmoscope capable of fluorescence lifetime imaging.

The present inventors have identified that hydroxyapatite (HAP), which is a highly insoluble basic form of calcium phosphate ($3Ca_3(PO_4)_2Ca(OH)_2$) and the principal mineral in bone and teeth, is a significant constituent of sub-retinal deposits (e.g., drusen), which can be observed in age-related macular degeneration (AMD) (7). HAP is marked by the additional hydroxide ions in its structure, is generally formed under more basic conditions than the mono- and dibasic calcium phosphates seen in tissue calcification, and is much less soluble and more stable than the other calcium phosphate forms. Furthermore, while amorphous calcium phosphate associated with the elastin layer of the Bruch's membrane and calcium ions can be present within the Bruch's membrane and the sub-RPE, the present inventors identified that the observed HAP is not primarily in the elastin layer of the BM, but is instead associated with sub-retinal deposits, such as drusen.

The present inventors identified compounds that bind HAP, fluoresce, and bind to sub-retinal deposits. These compounds permit earlier and accurate detection of such deposits and earlier detection of macular degeneration, such as AMD, and identification of individuals with an increased likelihood of developing macular degeneration such as AMD. The labels therefore can permit one to monitor the progression or regression of sub-retinal deposits by, for example, fluorescence ophthalmoscopy. The present inventors also identified that it is possible to detect HAP-containing deposits on the inner surface of the Bruch's membrane, above the inner collagenous layer, even at a stage when no deposits can be seen clinically or microscopically in post-mortem tissues.

In the present invention, tetracycline derivatives (including tetracycline itself) are used herein for a hydroxyapatite (HAP) label that binds substantially specifically to HAP and which allows its presence to be identified by means of a fluorescent signal. Tetracycline derivatives allow the presence of HAP to be identified because the tetracycline derivatives produce a signal that can be detected from outside the tissue in which the deposit is found and detectable by fluorescence lifetime imaging. Notably, a tetracycline derivative exhibits a change in the signal upon binding to the HAP, that being, the tetracycline exhibits a substantial increase in fluorescence lifetime upon binding to HAP, and thus, permitting HAP to be identified by fluorescence lifetime imaging methods known to the art.

Fluorescence-lifetime imaging is an imaging technique for producing, an image based on the differences in the exponential decay rate of the fluorescence from a fluorescent sample. It can be used as an imaging technique in confocal microscopy, two-photon excitation microscopy, fluorescence ophthalmoscopy, and multiphoton tomography.

Fluorescence lifetime imaging is an imaging technique that is able to distinguish between the different fluorophores in a biological sample. Due to the broad and overlapping emission spectra of many fluorophores or endogenous fluorophores, it is difficult to quantitatively measure the concentrations of these different species contributing to the fluorescence emission signal by spectral filtering alone. Fluorescence lifetime imaging is based on the fact that every fluorophore has a characteristic excited-state lifetime, $\tau$, or time for the molecule to decay from the excited electronic state to the ground state.

Excitation light sources can include arc lamps and lasers, laser diodes, externally modulated lamps, mode-locked lasers, spark gaps, supercontinuum lasers, and light emitting diode sources, and both single and multiple photon excitation sources. In another embodiment, use of a Ti-sapphire laser, Laser Diode (LD) or Light Emitting Diode Sources (LEDs) may be used. Excitation light frequencies may range from UV to IR and preferably in or near the visible frequency range. Pulsed excitation sources (lasers of all types, LEDs, or spark gaps) preferably exhibit pulse durations in the nanosecond to picosecond range, whereas amplitude modulated sources exhibit modulation frequencies in the range 100-fold larger or smaller than the expected emissive rate. Frequency domain data may also be collected by exciting with a train of picosecond-duration pulses at a MHz repetition rate, and measuring phase and modulation at effective modulation frequencies corresponding to multiples of the repetition rate.

Lifetime information can be measured either by time-domain or frequency-domain methods (4). In the time-domain technique, a pulsed excitation source is used to excite the fluorophore of interest in the biological sample. The subsequent time profile of the fluorescence emission is typically measured using time gating or time-correlated single photon-counting techniques, with the lifetime $\tau$ in the case of a single component determined from the time-dependent emission I(t) by the expression $I(t)=I_0 e^{-t/\tau}$. When multiple components with different lifetimes are present, the expression is more complex and the time-dependent emission data are typically fit to an assumed decay law to determine the lifetimes and fractional intensities (or preexponential factors) of the components. In frequency-domain, an amplitude-modulated excitation source is often employed. The lifetime of the fluorophore causes the emitted fluorescence signal to be modulated at the same frequency but with a phase delay and lower modulation relative to the excitation light. Measurement of this phase delay using phase-sensitive detection (such as a lockin amplifier) or other means will then give the value of the lifetime of a single component, $\tau$, by the relation $\tan \varphi = \omega\tau$, where $\varphi$ is the phase offset and $\omega$ is the modulation frequency. Similarly, the modulation m of the emission of a single component with respect to that of the excitation ($m=m_{emiss}/m_{exc}$) is also a simple function of the lifetime and modulation frequency: $m=(1+\omega^2\tau^2)^{-1/2}$. When multiple components with differing lifetimes are present these simple relations no longer hold, and phase delays and modulations measured at several different modulation frequencies are measured and also commonly fit to assumed decay laws to determine the lifetimes and fractions of the components.

Thus, for fluorescence lifetime imaging, one is collecting an image where the basis of contrast in the image comprises differences in the fluorescence lifetime(s) in the picture elements (pixels) making up the image, and not necessarily the fluorescence intensity or color. Therefore collecting the fluorescence lifetime image typically entails (in the time domain) collecting the time-dependent intensity for individual pixels or (in the frequency domain) phase and modulation data at multiple frequencies for individual pixels, then processing and displaying the lifetimes or lifetime-derived information as an image. In the case of multiple lifetime components being present, such lifetime-derived information may be an average lifetime computed by fitting the time decay of the pixel and obtaining the resulting lifetimes and fractions. In the frequency domain the average lifetime may also be computed but it is often convenient to highlight a subset of pixels in the image having a particular range of phase and modulation at some suitable frequency as indicating the lifetimes and fractions of the emitters present in those pixels. This is fast and convenient since in this case no complex fitting process need be implemented pixel by pixel, as it must be in the time domain.

Figure 3:
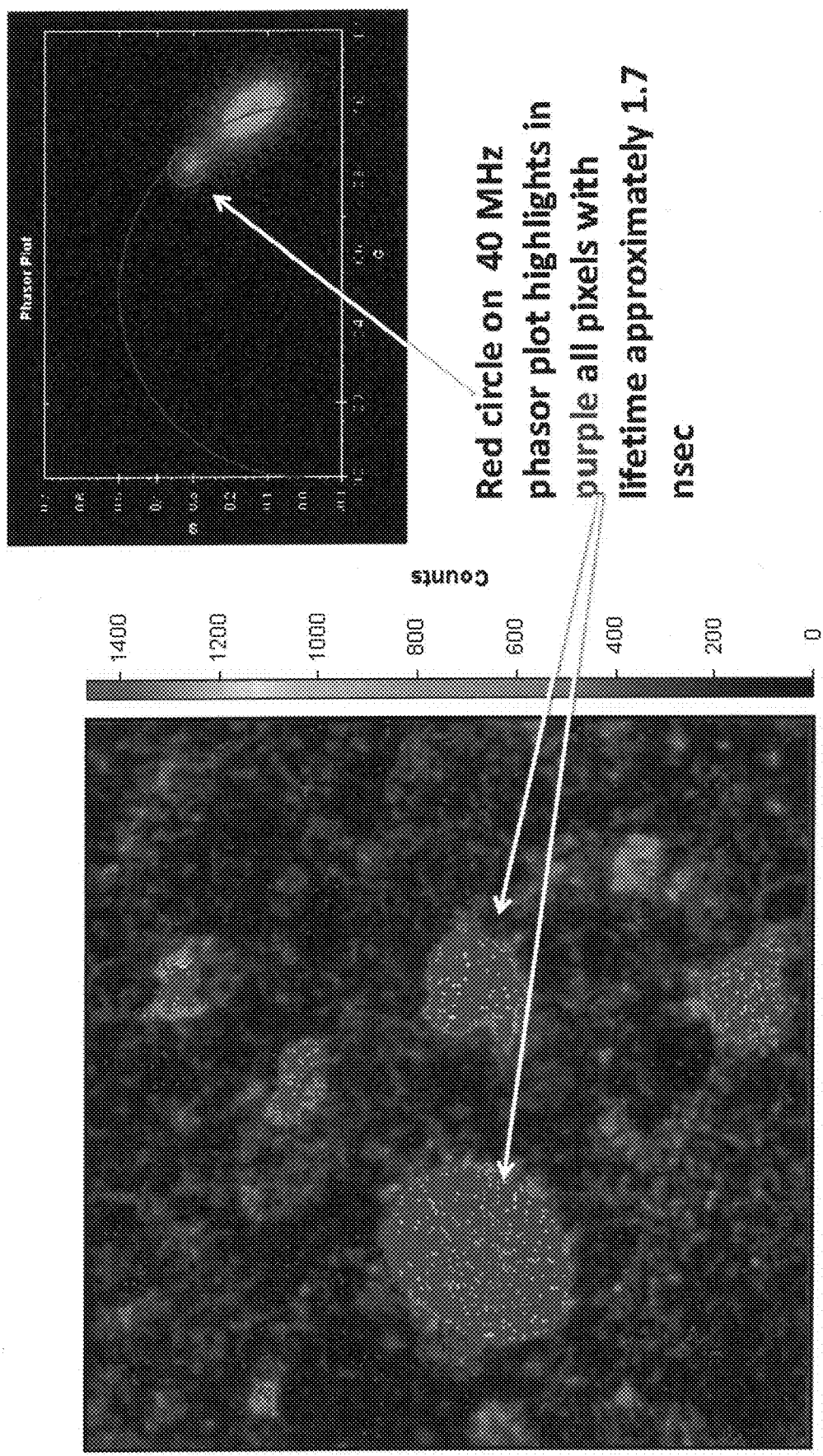
FIG. 3 shows that highlighting (purple) pixels which exhibit lifetimes (approximately 1.7 nsec) characteristic of chlortetracycline bound to HAP shows a high proportion are found within drusen.

While time domain and frequency domain methods provide equivalent information, the latter are frequently faster for imaging applications. For instance, the frequency domain method provides interpretable images in real time without the need to fit decays pixel by pixel by highlighting pixels that fall within the lifetime region of interest on the phasor plot (within the red circle) to easily identify the relevant regions of the image largely exhibiting the given lifetime (as shown in FIG. 3). Moreover, data can be simultaneously collected at several modulation frequencies simultaneously. In particular, the sample is excited using a pulsed laser emitting a train of picosecond pulses, such that the sample is effectively simultaneously excited with a "comb" of seven modulation frequencies that are harmonics of the pulse repetition frequency of 20 MHz. Finally, background of a particular lifetime may be directly suppressed in favor of a different lifetime in the frequency domain by use of a phase-sensitive detector like a lock-in amplifier, which may be useful for the present application.

The phasor plot of Redford and Clegg has been found effective wherein the measured phase and modulation at some suitable frequency, that being a range between 20-200 MHz, is used. The phasor plot uses polar coordinates, such that the phase angle $\Delta\varphi$ is the angle a vector anchored at the origin makes with the x-axis, and the vector's length equals m. For monoexponential decays $m=\cos \Delta\varphi$, and the points fall on the semicircular arc in FIG. 3 (inset): a lifetime of zero would map to 1, 0; and an infinite lifetime would map to 0, 0. For a multiexponential decay the points map to the interior of the arc, with the exact values calculable from the sine and cosine transforms of the components. Thus, an indicator that exhibited a monoexponential decay that changed monotonically with analyte concentration (e.g., due to simple collisional quenching) would map to points on the arc, whereas an indicator that exhibited different lifetimes when free or bound with analyte, would exhibit points in the interior of the arc as the fractional saturation varied from zero to 100%.

A commercially available software program plots different points on the phasor plot using the phases and modulations at a particular frequency of individual pixels in an image, and one can highlight areas in the image based on their lifetime properties by selecting a subset of points h a small circle to indicate the region of interest (in $\Delta\varphi$ and m space).

A fluorescence lifetime imaging device preferably comprises at least one light source that generates excitation light and having at least one detector that receives the detected light emitted from the sample. The light source preferably contains a semiconductor laser that emits pulsed excitation light, an adjusting apparatus being provided for adjusting the pulse repetition rate to the specific lifetime properties of the sample. For frequency and time domain measurements other light sources are well known to the art and useful for this invention, including amplitude-modulated (either internally or externally) lasers, light-emitting diodes, ion lasers, lamps, and mode-locked lasers. Similarly, numerous detectors are known to the art for frequency and time domain fluorescence measurements, including diodes, diode arrays, photomultiplier tubes, microchannel plate photomultipliers, avalanche photodiodes, and the like.

Preferably, an effective device uses fluorescence lifetime imaging microscopy (FLIM) or fluorescence lifetime imaging ophthalmoscopy (FLIO), the former of which is commercially available from several sources.

The terms "diagnosing" and "diagnosis" as used herein refer to methods by which the skilled artisan can estimate and even determine whether or not a subject is suffering from a given disease or condition. Along with diagnosis, clinical "prognosis" or "prognosticating" is also an area of great concern and interest. It is important to know the relative risk associated with particular conditions in order to plan the most effective therapy. If an accurate prognosis can be made, appropriate therapy, and in some instances less severe therapy or more effective therapy, for the patient can be chosen.

The tetracycline derivative, as a HAP label, may be formulated for delivery to the eye, for example for topical delivery, as an eye drop comprising an eye drop solution, or for intravitreal or other intraocular injection, or administered orally. Accordingly, it may also be formulated for systemic administration, for example as an intravenous injection or the like. Systemic administration may also be appropriate when the target tissue is in the eye. The HAP label may be combined with any appropriate pharmaceutically acceptable carrier, adjuvants, and/or excipients necessary or advantageous for the delivery method selected.

The term "pharmaceutically acceptable carrier" refers to sterile aqueous or nonaqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by flee inclusion of various antibacterial and antifungal agents such as paraben, chlorobutanol, phenol, sorbic acid and the like. It can also be desirable to include isotonic agents such as sugars, sodium chloride and the like.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents. The formulation can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Pharmaceutical preparations for oral administration can be obtained by combining the tetracycline derivative with suitable carriers. Suitable carriers are especially fillers, such as sugars, for example, lactose, saccharose, mannitol or sorbitol, cellulose preparations and/or calcium phosphates, for example, tricalcium phosphate or calcium hydrogen phosphate, and also binders, such as starch pastes, using, for example, corn, wheat, rice or potato starch, gelatin, tragacanth, methylcellulose and/or polyvinylpyrrolidone and, if desired, disintegrators, such as the above-mentioned starches, also carboxymethyl starch, cross-linked polyvinylpyrrolidone, agar or alginic acid or a salt thereof; such as sodium alginate. Coloring substances or pigments may be added, for example for the purpose of identification or to indicate different doses of the tetracycline derivative. Other orally administrable pharmaceutical preparations are dry-filled capsules made of gelatin, and also soft, sealed capsules made of gelatin and a plasticizer, such as glycerol or sorbitol.

Preparations for oral administration can be suitably formulated to give controlled release of the active compound. For buccal administration the compositions can take the form of tablets or lozenges formulated in conventional manner.

The formulations can be presented in unit-dose or multi-dose containers, for example sealed ampoules and vials, and can be stored in a frozen or freeze-dried (lyophilized) condition requiring only the addition of sterile liquid carrier immediately prior to use. In some embodiments the formulations are contained in containers that can dispense the solution in a drop wise manner. Such containers are particularly beneficial for administering eye drop formulations comprising the present labels and compositions.

Liquid preparations can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid).

The presently-disclosed subject matter is further illustrated by the following specific but non-limiting examples.

EXAMPLES

The fluorescence decay of several compounds known to bind to HAP was measured. The compounds were dissolved in pH 7.5 buffer solution and bound to HAP particles suspended in mineral oil. The compounds included tetracycline derivatives widely used as antibiotics including tetracycline (CAS number [60-54-8]), Chlortetracycline [57-62-5], doxycycline [17086-28-1] and minocycline [10118-90-8] both free in aqueous solution and bound to hydroxyapatite (Bio-Rad). These compounds have the key advantage that they are taken internally by humans and their toxicities (and safe dosages) are well established.

It was found that Doxycycline (Dox) and chlortetracycline (C1-Tet) exhibited substantial increases in lifetime upon binding compared to being dissolved in buffer: Dox ($<\tau>$0.6 increasing to 3.6 nsec upon binding); C1-Tet ($<\tau>$0.7 to 1.8 nsec). These lifetimes were measured in the frequency domain by phase fluorometry and the results are shown in FIG. 1. Importantly, the lifetime of both Dox and C1-Tet is much longer than retina autofluorescence background. Fluorescence imaging microscopy (FLIM) measurements of the living retina (5) indicated that the autofluorescence lifetimes were approximately 0.5 nsec. As such, the retina autofluorescence background lifetime was sufficiently different from the stained HAP with DOX and C1-Tex, providing a method for clearly defining HAP depositions using the tetracycline derivatives.

Figure 2:
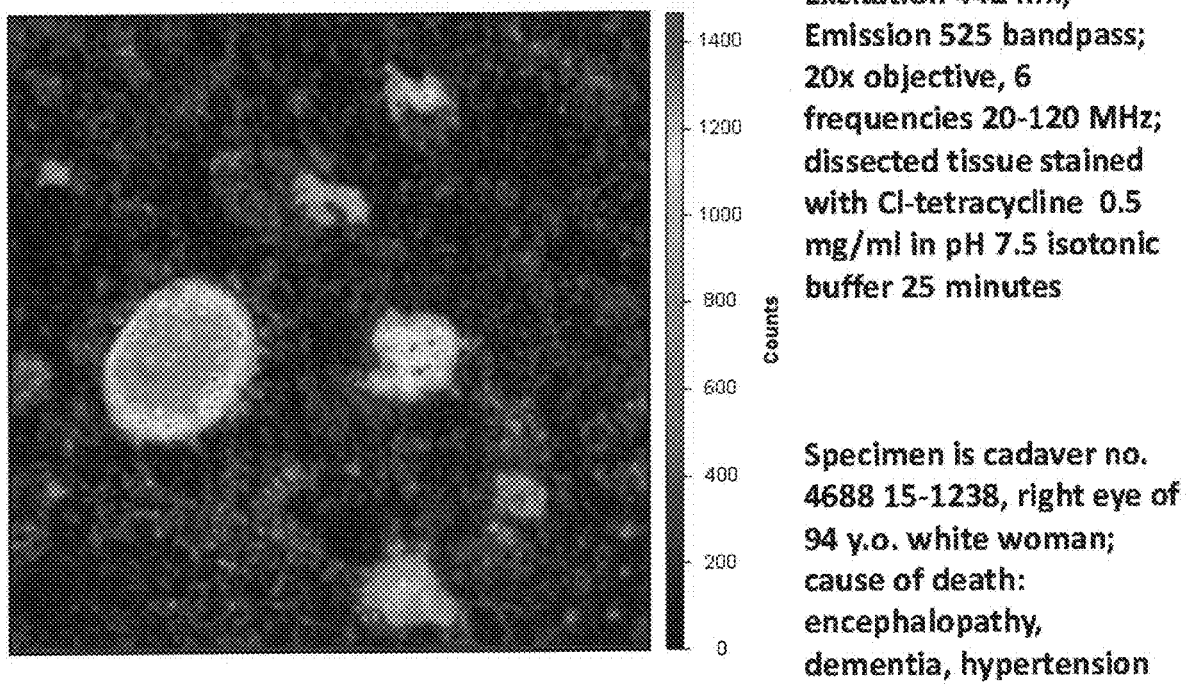
FIG. 2 shows a false colored fluorescence intensity image of a 94 year old human cadaver retina stained with Chlortetracycline.

FLIM mages were collected with excitation 443 nm, emission bandpass centered at 520 nm before and after staining with C1-Tet of a fixed retina (with neural retina and RPE mostly removed) from a 94 year old woman; her cause of death was listed as dementia, encephalopathy, and hypertension. A fluorescence intensity image is shown in FIG. 2 and showing some drusen. Also it was found that that sub-RPE deposits (drusen) stained with h chlortetracycline (CT) exhibited the same lifetime (approximately 1.6 nsec) as bound to HAP in a test tube, whereas most of the background fluorescence of these fixed tissues was approximately 0.6 nsec. Importantly, the tissue without staining exhibited almost no emission at a lifetime of 1.6 nsec, but it was also noted that such fixed tissue has different fluorescence background properties than live tissue. A small area of the C1 Tet-stained tissue was found that exhibited a 1.6 nsec lifetime that did not appear to be a deposit or drusen. However, the data of Schweitzer, et al., indicate that living retina has little or no emission in the 1.6 nsec range with similar spectral properties.

Figure 4:
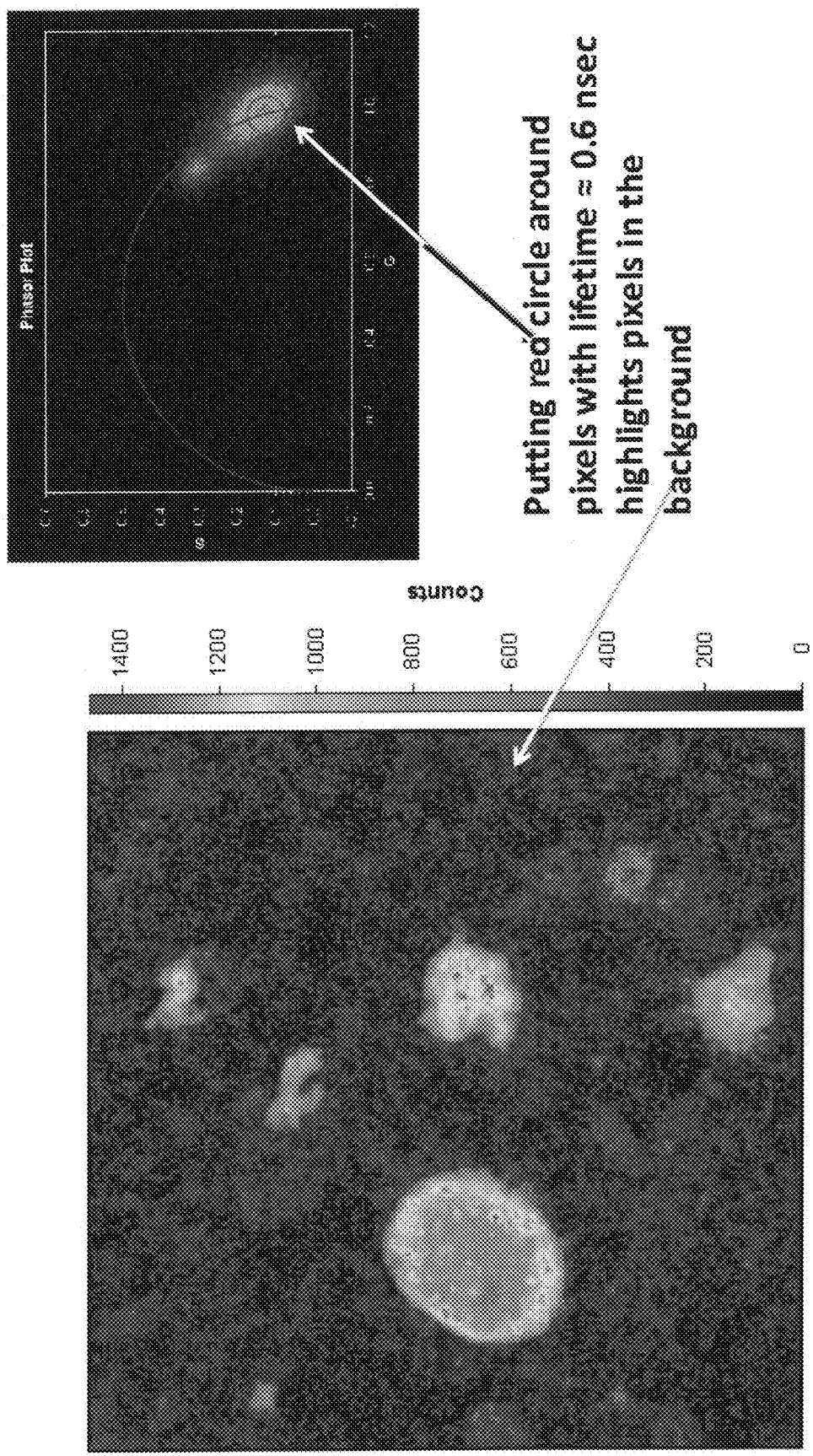
FIG. 4 shows that highlighting (purple) pixels which exhibit lifetimes (approximately 0.6 nsec) characteristic of retinal fluorescence background shows most are outside the drusen.

The FLIM images in the frequency domain are conveniently displayed as maps of pixels having phase and modulation (at a given frequency) that fall into a narrow range close to a particular lifetime. The phases and modulations of individual pixels are also plotted on polar coordinates in what is known as a "phasor plot," as shown in FIG. 3 in the upper right corner. The position of the pixel on the plot is at an angle with the x-axis equal to the phase angle, and a distance from the origin equal to the modulation, as discussed above. The pixels highlighted in purple (arrowed) are those that fall within the small red circle on the phasor plot roughly corresponding to a particular lifetime. The data in the FLIM images of FIG. 3 (256×256 pixels) were collected in a single data set in about a second. Thus, the highlighted pixels in purple whose phases and modulations are close to those for 1.7 nsec (the lifetime of C1-tetracycline bound to HAP) indicate the drusen. If the dotted and darkened circle is placed to select those pixels with a lifetime close to the expected background level of 0.6 nsec, pixels highlighted outside the drusen are visible, but not in the drusen as shown in FIG. 4.

Figure 5:
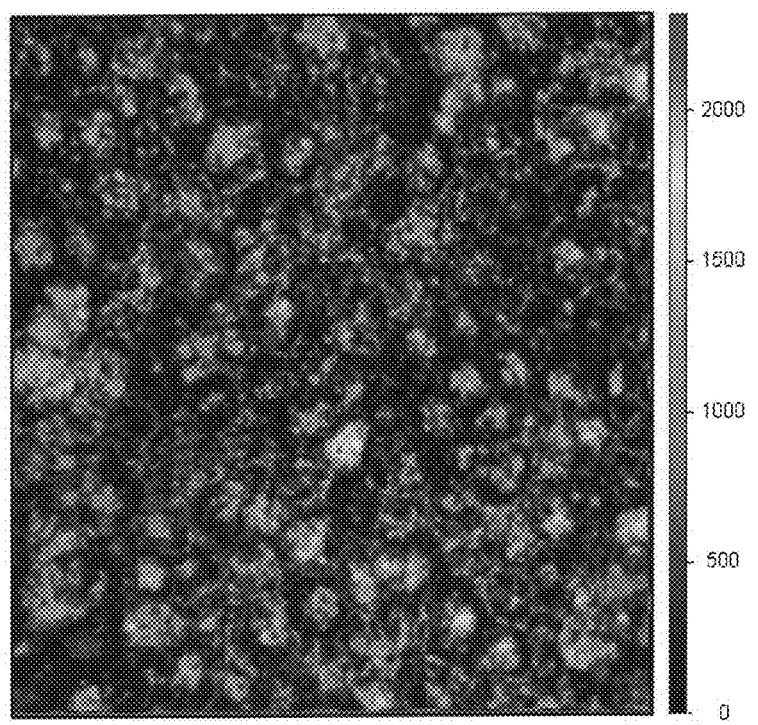
FIG. 5 shows an unstained fluorescence intensity image of a different portiere same specimen as shown in FIGS. 3 and 4.
Figure 6:
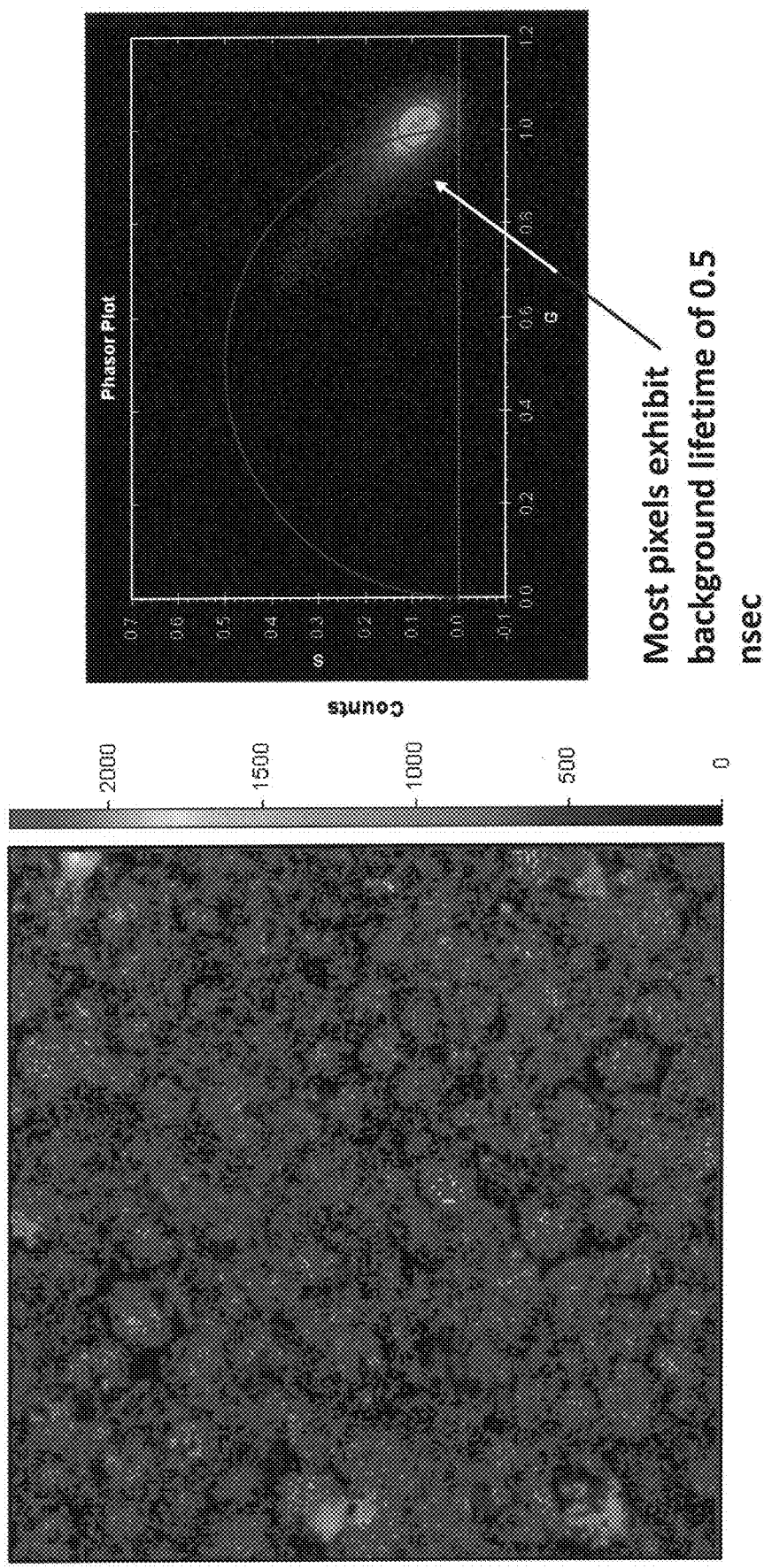
FIG. 6 shows that the unstained background pixels mainly have a very short lifetime of only about 0.5 nsec.

As shown in FIG. 5 which is the same tissue but in a different area and without staining, and FIG. 6, it is evident that the tissue showed most pixels in the background lifetime range (including RPE cells) with a background lifetime level of 0.5 nsec. However, only a few, isolated pixels with apparent lifetimes in the 1.7 nsec range are evident.

Figure 7:
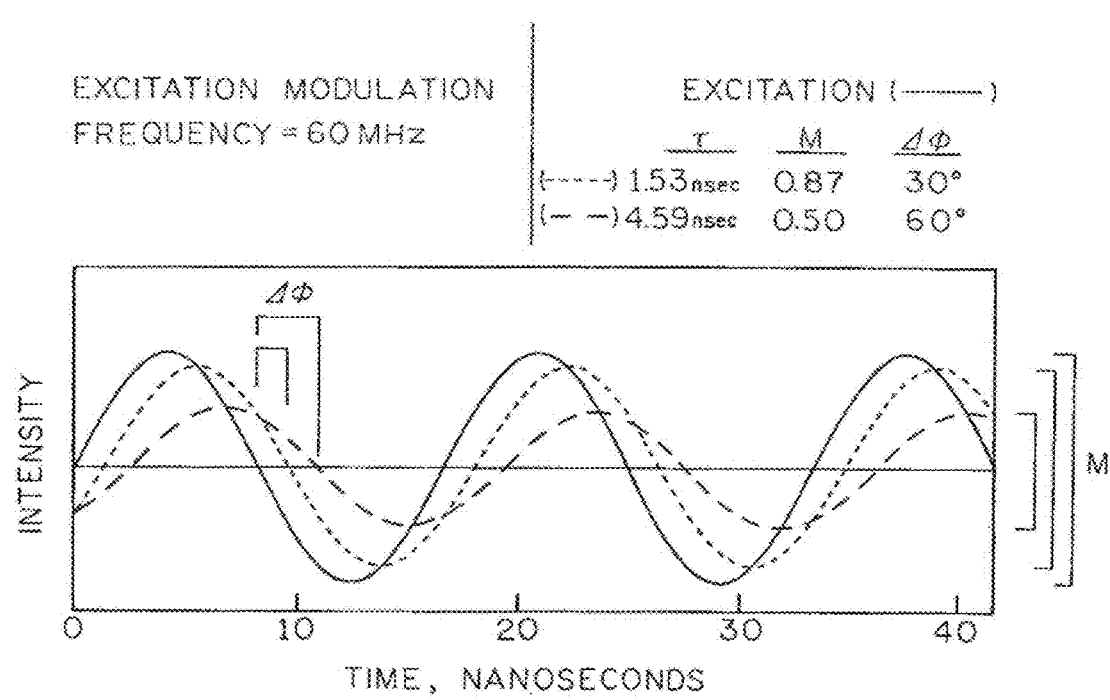
FIG. 7 shows the time-dependent intensity of modulated excitation (solid line) and fluorescence emission of fluorophores with 1.53 nsec (. . .) and 4.59 nsec (- - -) lifetimes, illustrating the phase difference ($\Delta\varphi$) and demodulation ratio m between excitation and sample fluorescence emission.

In the frequency domain (FD), the fluorophores are excited with modulated light at some frequency $\omega$; the fluorescence emission is phase-delayed by an angle $\varphi$ and demodulated by a factor m with respect to the excitation (see FIG. 7). The lifetime in FD measurements of a single class of emitters are simple functions of $\omega$ and $\varphi$ or m. When multiple lifetimes are present in TD, the time-dependent intensity data may be fit to a decay model and the accuracy judged by goodness-of-fit; in FD, φ and m are measured at multiple frequencies and the lifetimes and preexponential factors α of the components obtained by a comparable fitting procedure.

Figure 8:
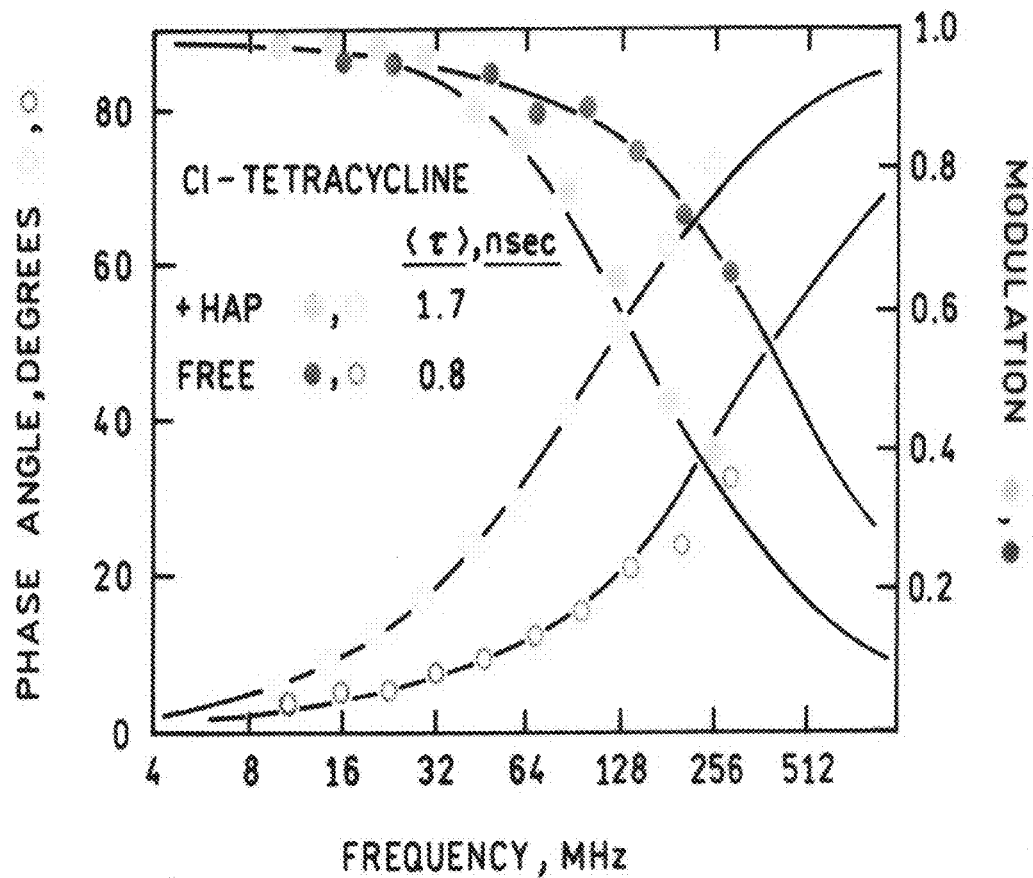
FIG. 8 shows lifetime of Cl-tetracycline in solution and bound to HAP.
Figure 9:
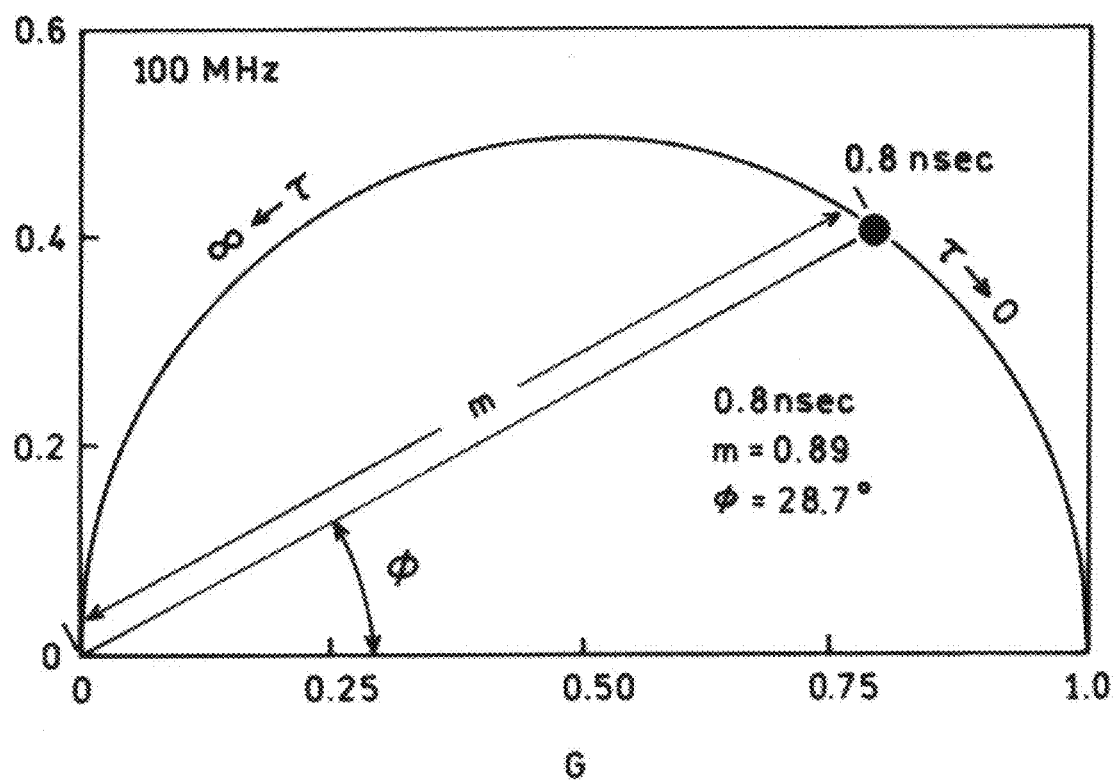

As shown in FIG. 8, phase angles φ (open circles) and modulations an (filled circles) were measured at frequencies from 10-300 MHz for C1-Tet free in buffer (light circles) and bound to hydroxyapatite (dark circles) to determine the lifetimes of C1-tetracycline in solution and also bound to HAP. The lines indicate the best two component fits to the data; the derived pixels are highlighted in the images whose φ's and m's fall in a particular range, which reflects their lifetime properties. The phasor plot of FIG. 9 maps the position of each pixel as x=m cos φ and y=m sin φ at some frequency ω. Thus pixels with x=0.82 and y=0.31 correspond to ≈1.7 nsec and x=0.95 and y=0.12 correspond to ≈0.6 nsec.

Figure 10:
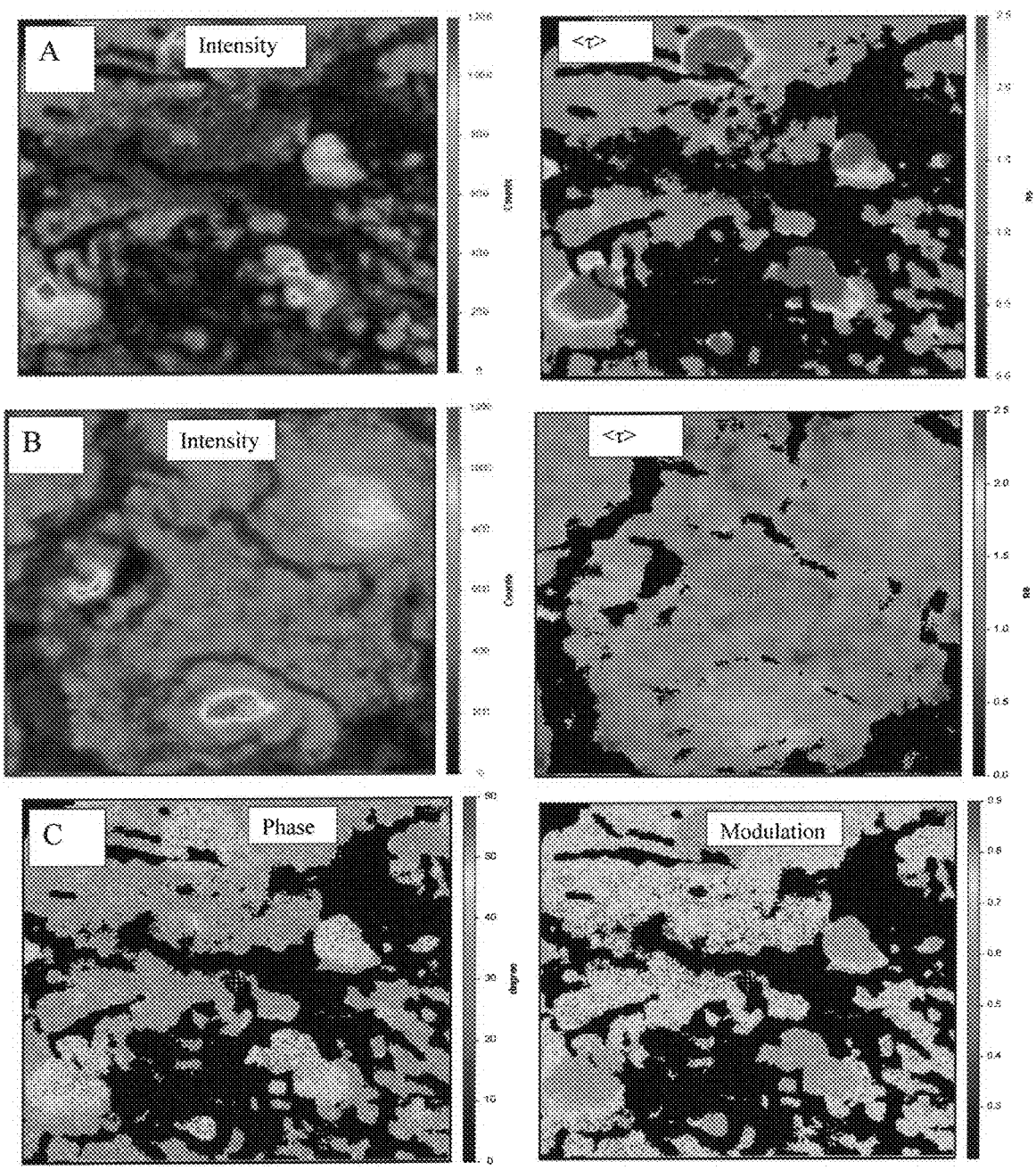
FIG. 10A shows Images of Average Lifetimes (Stained): Left panel is fluorescence intensity image of drusen, right panel pixel values color-coded with average lifetime. Bright areas fit $\tau1=1.91$ nsec, $\alpha1=0.95$; $\tau2=11.5$ nsec, $\alpha2=0.05$.
FIG. 10B shows Lifetime Images of Unstained Specimens wherein lifetime image shows low contrast of drusen with background. Bright areas fit $\tau1=0.89$ nsec, $\alpha1=0.87$; $\tau2=4.9$ nsec, $\alpha2=0.13$.
FIG. 10C shows images of Phases and Modulations (80 MHz). Images are color-coded of phase angle $\varphi$ (left) and modulation in (right) of same field as top row; note for HAP-bound C1-Tet, $\varphi\approx40$ degrees and m≈0.67 at 80 MHz.

Flat mounts of fixed retina preparations were stained from be previously discussed 94-year old female donor with Chlortetracycline (Amresco) and imaged by FD FLIM in an ISS Alba confocal fluorescence lifetime microscope with 473 nm excitation and 520 nm emission. The goal shown in FIG. 10 was to observe the differences in contrast between HAP in the drusen and the tissue background using three (3) FD FLIM display techniques that differ from the phasor plot technique illustrated in FIGS. 3, 4, and 6: 1) lifetime images using pixels that are false-colored based on their fraction-weighted average lifetimes tor both stained (FIG. 10A, right) and unstained images (FIG. 10B, right); plots of pixels false colored with their 2) phase (FIG. 10C, left) and modulation values (FIG. 10C, right) at a selected modulation, frequency (FIG. 10C). It is noted that others have used other means of displaying FLIM data, in particular coloring or highlighting pixels in an image based on preexponential-weighted lifetime averages, as well as preexponential factors or fractions of predetermined lifetimes.

The present approach of determining the lifetime of a signal offers some key advantages for early identification of sub-RPE deposition before vision loss due to AMD/AD. Initially, tetracyclines have been used for decades in humans, their absorption, distribution, metabolism, and excretion (ADME) is thoroughly known and their safety and modest risk factors are universally acknowledged. They can be given orally in safety, greatly simplifying their use in a screening assay. It is believed that doses given for AMD screening will be smaller than typical therapeutic doses since the drug is not being used to overcome resistant bacteria and with a single dose instead of a week-long course. As such, fluorescence lifetime-based imaging of tetracycline-family stained retinas with the use of a frequency-domain lifetime fluorescence ophthalmoscope offers substantial promise for rapid and convenient imaging of HAP in the living retina.

REFERENCES

The contents of all references cited herein are incorporated by reference herein for all purposes.
1. Sarks, et al (1999) *The British Journal of Ophthalmology*, 83, pp. 358-368.
2. Schweitzer, et al., "Towards metabolic mapping of the human retina," *Microscopy Research and Technique* 70, 410-419 (2007)).
3. Szmacinski, H., J. R. Lakowicz, et al. (1994). "Fluorescence lifetime imaging microscopy: homodyne technique using high-speed gated image intensifier," *Methods in Enzymology: Numerical computer Methods*. M. L. Johnson and L. Brand. New York, Academic Press. 240: 723-748).
4. J. R. Lakowicz, Principles of Fluorescence Spectroscopy, $2^{nd}$ Edition, Kluwer, 1999, Chapters 4 and 5.
5. Dysli, et al., *Invest. Ophthm Vis Sci* 55, 2106 (2014).
6. Becker et al. (2012) Fluorescence lifetime imaging-techniques and applications. *J of Microscopy*, V. 247 pp. 119-136.
7. Thompson, et al., (2015) "Identification of hydroxyapatite spherules provides new insight into subretinal pigment epithelial deposit formation in the aging eye, *Proc. Natl. Acad. Sciences USA* 112 (5) 1575-1570.

That which is claimed is:

1. A method for predicting or diagnosing age-related macular degeneration and/or Alzheimer's disease in a subject by detecting hydroxyapatite (HAP) deposits in the retina tissue of the subject, the method comprising:
   administering a tetracycline derivative to the subject in an amount sufficient for binding to any HAP deposits in the retina tissue of the subject;
   irradiating the retina tissue with electromagnetic radiation in an amount sufficient to excite the tetracycline derivative;
   scanning the retina tissue of the subject with a fluorescence lifetime imaging device and monitoring the lifetime of a fluorescent signal of any tetracycline derivative bound to HAP deposits;
   obtaining a profile of HAP deposits in the subject, wherein the HAP deposits bound to the tetracycline derivative exhibit a longer fluorescence lifetime compared to the fluorescence lifetime of the background tissue; and
   using the obtained profile to diagnose or predict age-related macular degeneration and/or Alzheimer's disease in the subject,
   wherein the tetracycline derivative is selected from the group consisting of chlortetracycline, demeclocycline, doxycycline, methacycline, oxycycline, anhydrochlortetracycline, anhydrotetracycline, and chelocardin.

2. The method according to claim 1, wherein the tetracycline derivative bound to the HAP deposits has a fluorescence lifetime from about 1.2 to about 6 nsec.

3. The method according to claim 1, wherein the background tissue has a fluorescence lifetime from about 0.2 to about 0.7 nsec.

4. The method according to claim 1, wherein the fluorescence lifetime imaging device uses frequency domain technology.

5. The method according to claim 1, wherein the profile is compared with a set of controls, wherein the set of controls comprise different levels of HAP deposits representing a particular stage of age-related macular degeneration and a control with no HAP deposits.

6. The method according to claim 1, wherein the tetracycline derivative is administered topically, orally or by injection.

7. The method according to claim 1, wherein the source of electromagnetic radiation is amplitude-modulated.

8. The method according to claim 1, wherein the scanning and monitoring entails collecting phase and modulation data at multiple frequencies for individual pixels.

9. The method according to claim 4, wherein the frequency domain technology highlights pixels that fall within a lifetime region of interest on a phasor plot to identify relevant regions of a fluorescence lifetime image.

10. The method according to claim 1, wherein a specific fluorescence lifetime is directly suppressed in favor of a different fluorescence lifetime by use of a phase-sensitive detector.

* * * * *